(12) United States Patent
Sakamoto et al.

(10) Patent No.: US 8,937,121 B2
(45) Date of Patent: Jan. 20, 2015

(54) CONDENSED HETEROCYCLIC COMPOUND AND COMPOSITION

(75) Inventors: Kei Sakamoto, Tokyo (JP); Satoshi Kiriki, Tokyo (JP); Tomonori Ogawa, Tokyo (JP); Masanobu Shinohara, Tokyo (JP)

(73) Assignee: Zeon Corporation, Tokyo (JP)

( * ) Notice: Subject to any disclaimer, the term of this patent is extended or adjusted under 35 U.S.C. 154(b) by 174 days.

(21) Appl. No.: 13/575,853

(22) PCT Filed: Jan. 28, 2011

(86) PCT No.: PCT/JP2011/051740
§ 371 (c)(1),
(2), (4) Date: Jul. 27, 2012

(87) PCT Pub. No.: WO2011/093443
PCT Pub. Date: Aug. 4, 2011

(65) Prior Publication Data
US 2012/0302675 A1 Nov. 29, 2012

(30) Foreign Application Priority Data
Jan. 29, 2010 (JP) ................................. 2010-019346

(51) Int. Cl.
| | |
|---|---|
| C08K 5/46 | (2006.01) |
| C08K 5/3417 | (2006.01) |
| C08L 13/00 | (2006.01) |
| C08L 19/00 | (2006.01) |
| C07D 279/34 | (2006.01) |
| C07D 209/88 | (2006.01) |

(52) U.S. Cl.
CPC ............ *C07D 279/34* (2013.01); *C07D 209/88* (2013.01); *C08K 5/3417* (2013.01); *C08K 5/46* (2013.01)
USPC .................... 524/83; 524/89; 544/35; 544/37; 546/102; 546/104; 546/107; 252/401; 252/402; 252/403

(58) Field of Classification Search
CPC ........ C09K 15/16; C09K 15/26; C09K 15/22; C08K 5/00; C08K 5/3437; C08K 5/47; C08K 5/3417; C07D 279/20; C07D 219/06; C07D 219/08; C07D 219/10; C07D 279/34; C07D 209/88
USPC ........... 524/83, 89; 544/35, 37; 546/102, 104, 546/107; 252/401, 402, 403
See application file for complete search history.

(56) References Cited

U.S. PATENT DOCUMENTS

| | | | |
|---|---|---|---|
| 2,815,343 A | 12/1957 | Horsley et al. | |
| 2,983,731 A | 5/1961 | Meis et al. | |
| 3,494,886 A | 2/1970 | Tholstrup et al. | |
| 3,625,963 A | 12/1971 | Capitant et al. | |
| 3,716,602 A | 2/1973 | Iwami et al. | |
| 3,803,140 A | 4/1974 | Cook et al. | |
| 3,822,284 A | 7/1974 | Werzner et al. | |
| 3,943,098 A | 3/1976 | Rody | |
| 4,061,631 A | 12/1977 | Rody | |
| 4,343,921 A | 8/1982 | Piestert | |
| 4,431,762 A | 2/1984 | Araki et al. | |
| 6,093,853 A | 7/2000 | Nakagome et al. | |
| 6,329,551 B1 | 12/2001 | Nakagome et al. | |
| 2002/0016508 A1 | 2/2002 | Nakagome et al. | |
| 2005/0159519 A1 | 7/2005 | Nakagome et al. | |
| 2008/0071014 A1 | 3/2008 | Ohishi et al. | |
| 2010/0273935 A1 | 10/2010 | Moritani | |

FOREIGN PATENT DOCUMENTS

| | | |
|---|---|---|
| CA | 1272722 A | 8/1990 |
| CN | 101472988 A | 7/2009 |
| CS | 221000 B1 | 3/1986 |

(Continued)

OTHER PUBLICATIONS

Chakrabarti et al., "Photo-Fries Rearrangements in N-Sulphonyl Carbazoles", Tetrahedron, 1989, vol. 45, No. 15, pp. 5059-5064.
Crevatin et al., "Photo-Fries Rearrangement of Carbazol-2-yl Sulfonates: Efficient Tool for the Introduction of Sulfonyl Groups into Polycyclic Aromatic Compounds", Helvetica Chimica Acta, 2006, 89 (6), pp. 1147-1157.
International Search Report, issued in PCT/JP2011/051740, dated, Mar. 15, 2011.
Matsumoto et al., "A Novel Reaction Promoted by Hydrogen Polyiodides (HI2n+1): Cyclization of 1-(1H-3-Indoly1)-4-(methylthio)-2-(p-tolylsulfonyl)-1,3-butadienes Accompanied with 1,2-Sulfonyl Migration", Chemistry Letters, 2002, 2, pp. 134-135.
Stokes et al., "Examination of the Mechanism of Rh2(II)-Catalyzed Carbazole Formation Using Intramolecular Competition Experiments", Journal of Organic Chemistry, 2009, 74 (17), pp. 6442-6451.
Yamamura et al., "Antioxidant Activities of Phenothiazines and Related Compounds: Correlation between the Antioxidant Activities and Dissociation Energies of O—H or N—H Bonds", Bulletin of the Chemical Society of Japan, 1997, 70 (2), pp. 413-419.

(Continued)

*Primary Examiner* — Kriellion Sanders
(74) *Attorney, Agent, or Firm* — Birch, Stewart, Kolasch & Birch, LLP

(57) ABSTRACT

A condensed heterocyclic compound which is shown by the following formula (I) and a composition containing an (a) organic material and (b) at least one type of the condensed heterocyclic compound are provided.

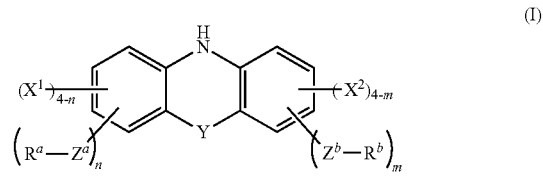

(I)

(Y indicates a chemical single bond, —S(=O)—, or —$SO_2$—. $R^a$ and $R^b$ indicate substitutable $C_1$ to $C_{30}$ organic groups. $Z^a$ and $Z^b$ indicate chemical single bonds or —$SO_2$—. $X^1$ and $X^2$ indicate hydrogen atoms etc. n and m respectively independently indicate integers of 0 to 2, where one of n and m is not 0).

13 Claims, No Drawings

(56) References Cited

FOREIGN PATENT DOCUMENTS

| | | |
|---|---|---|
| EP | 0 334 500 A1 | 9/1989 |
| FR | 1442299 | 6/1966 |
| GB | 1140089 | 1/1969 |
| GB | 1 347 141 A | 2/1974 |
| GB | 2001648 A | 2/1979 |
| JP | 46-41445 | 12/1971 |
| JP | 47-19088 | 6/1972 |
| JP | 48-28761 | 9/1973 |
| JP | 49-74179 | 7/1974 |
| JP | 55-69672 A | 5/1980 |
| JP | 57-115435 A | 7/1982 |
| JP | 58-17158 A | 2/1983 |
| JP | 60-155165 A | 8/1985 |
| JP | 04-174886 A | 6/1992 |
| JP | 8-301846 A | 11/1996 |
| JP | 9-53070 A | 2/1997 |
| JP | 10-298551 A | 11/1998 |
| JP | 11-21411 A | 1/1999 |
| JP | 2008-031330 A | 2/2008 |
| JP | 2008-291083 A | 12/2008 |
| JP | 2009-007491 A | 1/2009 |
| JP | 2009-084514 A | 4/2009 |
| JP | 2010-174217 A | 8/2010 |
| JP | 2011-001428 A | 1/2011 |
| PL | 160661 B1 | 4/1993 |
| WO | WO 88/02007 A2 | 3/1988 |
| WO | WO 02/081432 A2 | 10/2002 |
| WO | WO 2006/001299 A1 | 1/2006 |
| WO | WO 2007/020932 A1 | 2/2007 |

OTHER PUBLICATIONS

European Office Action dated Jun. 18, 2013 issued in European Patent Application No. 11 737 153.4.
J. I. G. Cadogan et al.; Nitrene-induced cyclisations accompanied by rearrangement in thermolyses of aryl-2-azidophenyl sulphones . . . ; Journal of the Chemical Society; Perkin Transacations 1; No. 16; 1976; p. 1749.
Jan Bergman et al.; Synthesis of carbazoles related to carbazomycin, hyellazole and ellipticine; Tetrahedron; vol. 44; No. 16; 1998; pp. 5215-5228.
Nathan L. Smith; Research Article Cyanoethylation of Some Carbazole Derivatives; Journal of the American Chemical Society; vol. 72; No. 9; 1950; pp. 4313-4314.
Sergio M. Bonesi et al.; A study of substituent effect of 1 H and 13 C NMR spectra of N- and C-substituted carbazoles . . . ; Journal of Heterocyclic Chemistry; vol. 41; No. 2; 2004; pp. 161-171.
Shoji Matsumoto et al.; A novel reaction promoted by hydrogen polyiodides . . . ; Chemistry Letters, Chemical Society of Japan; vol. 2; 2002; pp. 134-135.
Ulf Pindur et al.; Cycloadditions of pyrano 3,4-bindol-3-ones with 1,2-bis-acceptor . . . ; Heterocycles International Journal for Reviews and Communications in Heterocyclic Chemistry; vol. 31; No. 10; 1990; pp. 1751-1761.
Database Abstract, "10H-Phenothiazine, 2, 8-diphenyl-", Database Accession No. 947731.93-3, Sep. 24, 2007, XP-002711931.
Database Abstract, "Derivatives of thiodiphenylamine", Gazzetta Chimica Italiana, vol. 62, Database Accession No. 41851, 1932, pp. 175-189, XP-002711930.
Database Abstract, "New rearrangement of 10-arenesulfonylphenothiazines", CAPLUS, Database Accession No. 443284, 1976, XP-002711929.
Extended European Search Report, dated Sep. 12, 2013, for Patent Application No. 11737153.4.
Extended European Search Report, dated Sep. 24, 2013, for Patent Application No. 11737154.2.
Hallberg et al., "1,2-Didehydrophenothiazines: Preparation of 1-Alkyl and 1-Aryl-substituted Phenothiazines by Lithium-directed Alkylation", J.Chem. Soc. Perkin Trans., vol. 1, 1985, pp. 969-971.
Katritzky et al., "Specific Synthesis of 1-Substituted Phenothiazines Using Carbon Dioxide Protection of the NH Group During Lithiation", Papers, Mar. 1988, pp. 215-217.
Lafferty et al., "The Synthesis of Phenothiazines. VII.1 Methyl-and Arylsulfonylation of Phenothiazine and Its 10-Substituted Derivatives", The Journal of Organic Chemistry, vol. 27, No. 4, Apr. 1, 1962, pp. 1346-1351.
Madrid et al., "Synthesis and antitubercular activity of phenothiazines with reduced binding to dopamine and serotonin receptors", Bioorganic & Medicinal Chemistry Letters, vol. 17, 2007, pp. 3014-3017.
File Registry on STNm RN 876487-30-8, Entered STN: Mar. 12, 2006.
Heterocycles, "An International Journal for Reviews and Communications in Heterocyclic Chemistry", vol. 31, No. 10 (1990) pp. 1751-1761.

CONDENSED HETEROCYCLIC COMPOUND AND COMPOSITION

TECHNICAL FIELD

The present invention relates to a novel condensed heterocyclic compound which can impart high processing stability and heat resistance, and long life to a polymer or other organic material which is susceptible to oxidation, heat, or light induced breakdown and to a composition which contains an organic material and that condensed heterocyclic compound.

BACKGROUND ART

Polymers and other organic materials are susceptible to degradation by oxidation due to heat etc. if left as they are, so to improve their heat resistances, various antiaging agents are added to obtain heat resistances according to the particular objectives. As such antiaging agents, for example, diphenylamine-based antiaging agents which are described in Patent Documents 1 to 3 are widely known.

In this regard, in recent years, polymers and other organic materials have been increasingly used at tougher high temperatures. For example, for the rubber materials which are used around the engines of automobiles, the temperatures in the engine compartments have been rising as a general trend due to the higher outputs of automobile engines and the appearance of low pollution engines etc. Therefore, the rubber materials which are used in their surroundings are required to exhibit better heat resistance.

Therefore, as one measure for achieving this object, development of a new antiaging agent which has a better effect than conventional diphenylamine-based antiaging agents has been desired.

PRIOR ART DOCUMENTS

Patent Documents

Patent Document 1: Japanese Patent Publication No. 9-53070
Patent Document 2: Japanese Patent Publication No. 10-298551
Patent Document 3: Japanese Patent Publication No. 11-21411

SUMMARY OF THE INVENTION

Problem to be Solved by the Invention

The present invention was made in consideration of the above situation and has as its object the provision of a novel condensed heterocyclic compound which is able to be synthesized easily and has a superior antiaging action on organic materials which are susceptible to oxidation, heat, or light induced breakdown and of a composition which contains an organic material and that condensed heterocyclic compound.

Means for Solving the Problems

The inventors engaged in intensive research for achieving the above object and as a result discovered novel condensed heterocyclic compounds which can impart extremely superior heat stability or other property to polymers and other organic materials.

Therefore, according to a first aspect of the present invention, there are provided condensed heterocyclic compounds of the following (1) to (5).

(1) The condensed heterocyclic compound which is shown in the following formula (I).

[Chemical Formula 1]

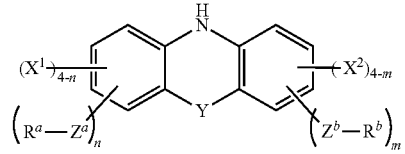

(I)

[where, in the formula, Y indicates a chemical single bond, —S(=O)—, or —SO$_2$—.
R$^a$ and R$^b$ respectively independently indicate substitutable C$_1$ to C$_{30}$ organic groups.
Z$^a$ and Z$^b$ respectively independently indicate chemical single bonds or —SO$_2$—.
X$^1$ and X$^2$ respectively independently indicate hydrogen atoms, halogen atoms, substitutable C$_1$ to C$_{10}$ alkyl groups, cyano groups, nitro groups, —OR$^1$, —O—C(=O)—R$^1$, —C(=O)—OR$^1$, —O—C(=O)—OR$^1$, —NR$^2$(R$^3$), —NR$^2$—C(=O)—R$^1$, —C(=O)—NR$^2$(R$^3$), or —O—C(=O)—NR$^2$(R$^3$).
Here, R$^1$, R$^2$, and R$^3$ respectively independently indicate hydrogen atoms or substitutable C$_1$ to C$_{20}$ organic groups.
n and m respectively independently indicate integers of 0 to 2, where either of n and m is not 0.
Further, when n and/or m is 2, two of R$^a$ and two of R$^b$ may be the same as each other or may be different.]

(2) The condensed heterocyclic compound as set forth in (1), wherein in the formula (I), R$^a$ and R$^b$ respectively independently indicate substitutable linear or branched C$_1$ to C$_{20}$ alkyl groups or substitutable phenyl groups.

(3) The condensed heterocyclic compound as set forth in (2), wherein in the formula (I), R$^a$ and R$^b$ respectively independently indicate α-methylbenzyl groups, α,α-dimethylbenzyl groups, t-butyl groups, phenyl groups, or 4-methylphenyl groups.

(4) The condensed heterocyclic compound as set forth in any one of (1) to (3), which is an antiaging agent.

According to a second aspect of the present invention, there are provided the compositions of the following (5) to (9):

(5) The composition which contains (a) an organic material and (b) at least one type of condensed heterocyclic compound as set forth in any one of (1) to (4).

(6) The composition as set forth in (5), wherein the ingredient (a) is a synthetic polymer.

(7) The composition as set forth in (5) or (6), wherein the ingredient (a) is a synthetic rubber.

(8) The composition as set forth in any one of (5) to (7), wherein the ingredient (a) is acrylic rubber or hydrogenated nitrile rubber.

(9) The composition as set forth in any one of (5) to (8), wherein the ingredient (a) is acrylic rubber.

Effects of the Invention

According to the present invention, there are provided a novel condensed heterocyclic compound which can impart high processing stability and heat resistance, and long life to a polymer or other organic material which is susceptible to oxidation, heat, or light induced breakdown and a composition which contains an organic material and that condensed heterocyclic compound.

DESCRIPTION OF EMBODIMENTS

Below, the present invention will be explained divided into 1) condensed heterocyclic compounds and 2) compositions which contain organic materials and the condensed heterocyclic compounds.

1) Condensed Heterocyclic Compounds

A first aspect of the present invention is a condensed heterocyclic compound which is shown by the above formula (I).

Where, in formula (I), Y indicates a chemical single bond, —S(=O)—, or —SO$_2$—. In formula (I), —S(=O)— and —SO$_2$— are preferable, and —SO$_2$— is more preferable.

In formula (I), R$^a$ and R$^b$ respectively independently indicate substitutable C$_1$ to C$_{30}$ organic groups.

As the C$_1$ to C$_{30}$ organic groups which form the R$^a$ and R$^b$, C$_1$ to C$_{30}$ alkyl group such as methyl group, ethyl group, n-propyl group, isopropyl group, n-butyl group, isobutyl group, sec-butyl group, t-butyl group, n-pentyl group, n-hexyl group, n-heptyl group, n-octyl group, n-nonyl group, and n-decyl group; C$_3$ to C$_{30}$ cycloalkyl group such as cyclopropyl group, cyclopentyl group, cyclohexyl group, cycloheptyl group, and cyclooctyl group; C$_6$ to C$_{30}$ aryl group such as phenyl group, biphenyl group, naphthyl group, and anthranyl group; C$_1$ to C$_{30}$ alkoxy group such as methoxy group, ethoxy group, n-propoxy group, isopropoxy group, n-butoxy group, isobutoxy group, sec-butoxy group, t-butoxy group, n-pentyloxy group, and n-hexyloxy group; etc. may be mentioned.

Further, the above-mentioned organic groups which form R$^a$ and R$^b$ may have substituents. The positions of the substituents may be made any positions.

As the substituents of the organic groups, when the organic groups are alkyl groups, a halogen atom such as fluorine atom, chlorine atom, and bromine atom; C$_1$ to C$_{10}$ alkoxy group such as methoxy group, ethoxy group, and isopropoxy group; nitro group; cyano group; substitutable phenyl group such as phenyl group, 4-methylphenyl group, and 2-chlorophenyl group; etc. may be mentioned.

When the organic groups are cycloalkyl groups and aryl groups, a halogen atom such as fluorine atom, chlorine atom, and bromine atom; C$_1$ to C$_{10}$ alkoxy group such as methoxy group, ethoxy group, and isopropoxy group; nitro group; cyano group; C$_1$ to C$_{10}$ alkyl group such as methyl group, ethyl group, and t-butyl group; etc. may be mentioned.

Further, when the organic groups are alkoxy groups, a halogen atom such as fluorine atom, chlorine atom, and bromine atom; nitro group; cyano group; etc. may be mentioned.

Note that, in the present invention, when the organic groups which form the R$^a$ and R$^b$ have substituents, the numbers of carbon atoms of organic groups are deemed to not include the numbers of carbon atoms of the substituents. That is, the organic groups which form the R$^a$ and R$^b$ should have numbers of carbon atoms, minus the carbon atoms which are included in the substituents, of 1 to 30 in range. For example, when the organic group which form the R$^a$ and R$^b$ is methoxyethyl group, the numbers of carbon atoms of the organic groups become 2. That is, in this case, since the methoxy group is substituent, so the numbers of carbon atoms of the organic groups become the numbers of carbon atoms minus those of methoxy group as the substituent.

In the present invention, as R$^a$ and R$^b$, respectively independently substitutable linear or branched C$_1$ to C$_{20}$ alkyl groups, substitutable phenyl groups and substitutable naphthyl groups are preferable, while substitutable linear or branched C$_2$ to C$_8$ alkyl groups and substitutable phenyl groups are more preferable.

As preferable specific examples of such organic groups which form the R$^a$ and R$^b$, an α-methylbenzyl group, α,α-dimethylbenzyl group, t-butyl group, phenyl group or 4-methylphenyl group, etc. may be mentioned, Among these as well, an α,α-dimethylbenzyl group or 4-methylphenyl group is particularly preferable. Note that, these may be respectively made independent.

In the formula (I), Z$^a$ and Z$^b$ respectively independently indicate chemical single bonds or —SO$_2$—. Chemical single bonds are preferable.

In the formula (I), X$^1$ and X$^2$ respectively independently indicate hydrogen atoms, halogen atoms, substitutable C$_1$ to C$_{10}$ alkyl groups, cyano groups, nitro groups, —OR$^1$, —O—C(=O)—R$^1$, —C(=O)—OR$^1$, —O—C(=O)—OR$^1$, —NR$^2$(R$^3$), —NR$^2$—C(=O)—R$^1$, —C(=O)—NR$^2$(R$^3$), or —O—C(=O)—NR$^2$(R$^3$).

As the halogen atoms which form the X$^1$ and X$^2$, a fluorine atom, chlorine atom, bromine atom, etc. may be mentioned.

As the C$_1$ to C$_{10}$ alkyl groups of the substitutable C$_1$ to C$_{10}$ alkyl groups, a methyl group, ethyl group, propyl group, isopropyl group, n-butyl group, isobutyl group, t-butyl group, n-pentyl group, n-hexyl group, n-heptyl group, n-octyl group, n-nonyl group, n-decyl group, etc. may be mentioned.

As the substituents of the C$_1$ to C$_{10}$ alkyl groups, halogen atom such as fluorine atom, chlorine atom, and bromine atom; alkoxy group such as methoxy group, ethoxy group, n-propoxy group, isopropoxy group, n-butoxy group, and t-butoxy group; nitro group; cyano group, etc. may be mentioned.

R$^1$, R$^2$, and R$^3$ respectively independently express hydrogen atoms or substitutable C$_1$ to C$_{20}$ organic groups, while all of R$^1$, R$^2$, and R$^3$ being hydrogen atoms is preferable.

As the C$_1$ to C$_{20}$ organic groups of the substitutable C$_1$ to C$_{20}$ organic groups which form the R$^1$, R$^2$, and R$^3$, C$_1$ to C$_{20}$ alkyl group such as methyl group, ethyl group, n-propyl group, isopropyl group, n-butyl group, isobutyl group, t-butyl group, n-pentyl group, n-hexyl group, n-heptyl group, n-octyl group, n-nonyl group, and n-decyl group; C$_3$ to C$_{20}$ cycloalkyl group such as cyclopropyl group, cyclopentyl group, cyclohexyl group, cycloheptyl group, and cyclooctyl group; C$_6$ to C$_{20}$ aryl group such as phenyl group, naphthyl group, and anthranyl group; C$_1$ to C$_{20}$ alkoxy group such as methoxy group, ethoxy group, n-propoxy group, isopropoxy group, n-butoxy group, isobutoxy group, sec-butoxy group, t-butoxy group, n-pentyloxy group, and n-hexyloxy group; etc. may be mentioned.

As the substituents of the organic groups which form the R$^1$, R$^2$, and R$^3$, ones similar to those listed as substituents of the organic groups which form the R$^a$ and R$^b$ explained above may be mentioned.

Among these as well, as X$^1$ and X$^2$, from the viewpoints of ease of acquisition etc., both being hydrogen atoms is preferable.

In the formula (I), n and m respectively independently indicate integers of 0 to 2, where either of n and m is not 0. n and m respectively independently being 0 or 1 (where either of n and m is not 0) is preferable, while n and m being 1 is more preferable.

Further, when n and/or m is 2, two of R$^a$ and two of R$^b$ may be the same or different.

As the condensed heterocyclic compound of the present invention, any of the compounds which are expressed by the following formulae (II) to (IX) is preferable.

[Chemical Formula 2]

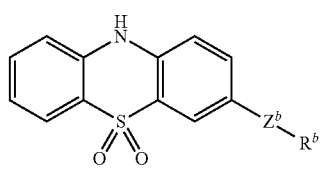

(II)

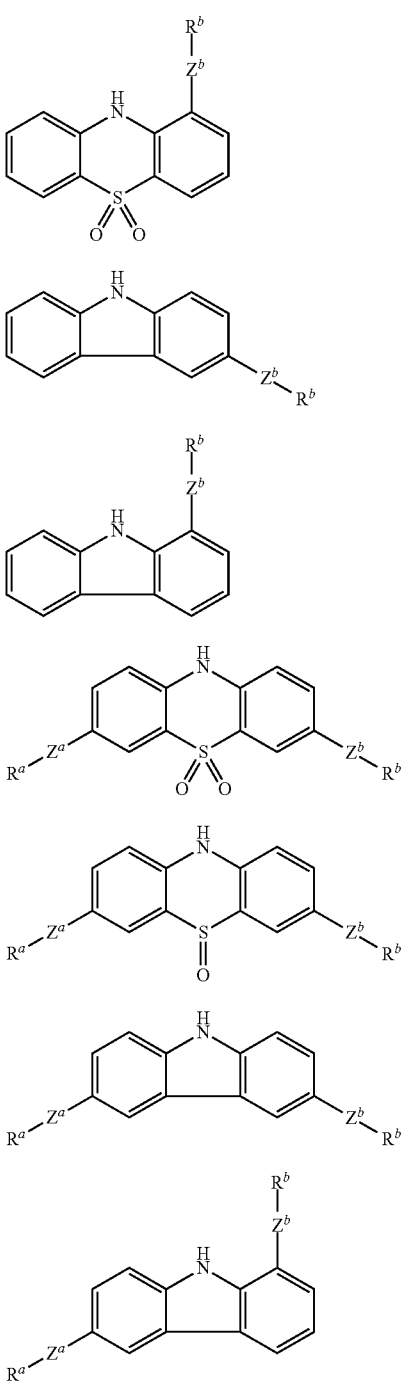

(in the above formulae, $R^a$, $R^b$, $Z^a$, and $Z^b$ express the same meanings as the formula (I).)

Among the compounds which are expressed by the formulae (II) to (IX) as well, compounds which are expressed by the formulae (II), (VI), and (VII) are more preferable, compounds which are expressed by the formulae (VI) and (VII) are furthermore preferable, and compounds which are expressed by the formula (VI) are particularly preferable.

Further, among the general formulae (II) to (IX), the compound in which —$Z^a$—$R^a$ and —$Z^b$—$R^b$ respectively independently are α-methylbenzyl groups, α,α-dimethylbenzyl groups, t-butyl groups, phenylsulfonyl groups, or 4-methylphenylsulfonyl groups is more preferable, the compound in which —$Z^a$—$R^a$ and —$Z^b$—$R^b$ are α,α-dimethylbenzyl groups is particularly preferable.

(Method of Production of Condensed Heterocyclic Compound Expressed by Formula (I))

Among the compounds which are expressed by the formula (I), compounds where Y is —$SO_2$— can be produced by applying the known method of production of phenothiazine-based compounds to obtain a compound of the formula (I) where Y is S, then oxidizing the obtained compound.

Further, among the compounds which are expressed by the formula (I), compounds where Y is a single bond can be produced by applying the known method of production of a carbazole-based compound.

Further, compounds which are expressed by the formula (I) can be obtained by using compounds which are expressed by the following formula (2) [phenothiazine ($Y^1$=S) and carbazole ($Y^1$=chemical single bond)] as starting materials and using a known reaction method to introduce substituents (—$Z^a$—$R^a$ and —$Z^b$—$R^b$) into the 1-position, 3-position, 6-position, and/or 8-position of the aromatic rings of the formula (2) and, when $Y^1$=S, making $Y^1$ into —$SO_2$— by oxidation. Note that, the compounds which are expressed by the formula (2) are nonsubstituted, but compounds which have the substituents ($X^{1a}$, $X^{2a}$) at any positions of the aromatic rings may also be used as starting materials. Here, $X^{1a}$ and $X^{2a}$ respectively indicate the atoms and substituents other than hydrogen atoms which form the above-mentioned $X^1$ and $X^2$.

[Chemical Formula 3]

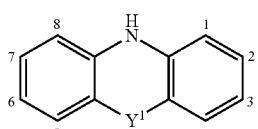

(2)

(in the formula (2), $Y^1$ is S or a chemical single bond)

As the reaction method which introduces one or more substituents (—$Z^a$—$R^a$, —$Z^b$—$R^b$) at the 1-position, 3-position, 6-position, and/or 8-position of the aromatic rings in the formula (2), for example, a reaction which causes the formation of a carbon-carbon bond at the carbon atoms of the 1-position, 3-position, 6-position, and/or 8-position of the aromatic rings in the formula (2) (this reaction method will be referred to as the "reaction method α"), a reaction which causes the formation of a carbon-$SO_2$ bond at the carbon atoms of the 1-position, 3-position, 6-position, and/or 8-position of the aromatic rings in the formula (2) (this reaction method will be referred to as the "reaction method β"), a reaction which causes the formation of a carbon-sulfur bond at the carbon atoms of the 1-position, 3-position, 6-position, and/or 8-position of the aromatic rings in the formula (2) (this reaction method will be referred to as the "reaction method γ"), etc. may be mentioned.

Below, the method of production of the compound which is expressed by the formula (I) will be explained in detail while using as an example the case of using compounds which are expressed by the formula (2) as a starting material and using the methods of the above-mentioned reaction method α, reaction method β, and reaction method γ.

[A. Method of Production (1) Using Reaction Method α]

The reaction formula of the method of production (1) which uses the reaction method α is shown below. Note that, in the following reaction formula, among the compounds which are expressed by the formula (I), the case where Y is a chemical single bond or —SO$_2$—, n or m is 0, and —Z$^a$—R$^a$ or —Z$^b$—R$^b$ is a group which is indicated by the formula: —C(CH$_3$)(r)—Ar (wherein, r indicates a hydrogen atom or alkyl group, and Ar indicates a substitutable phenyl group) is illustrated.

[Chemical Formula 4]

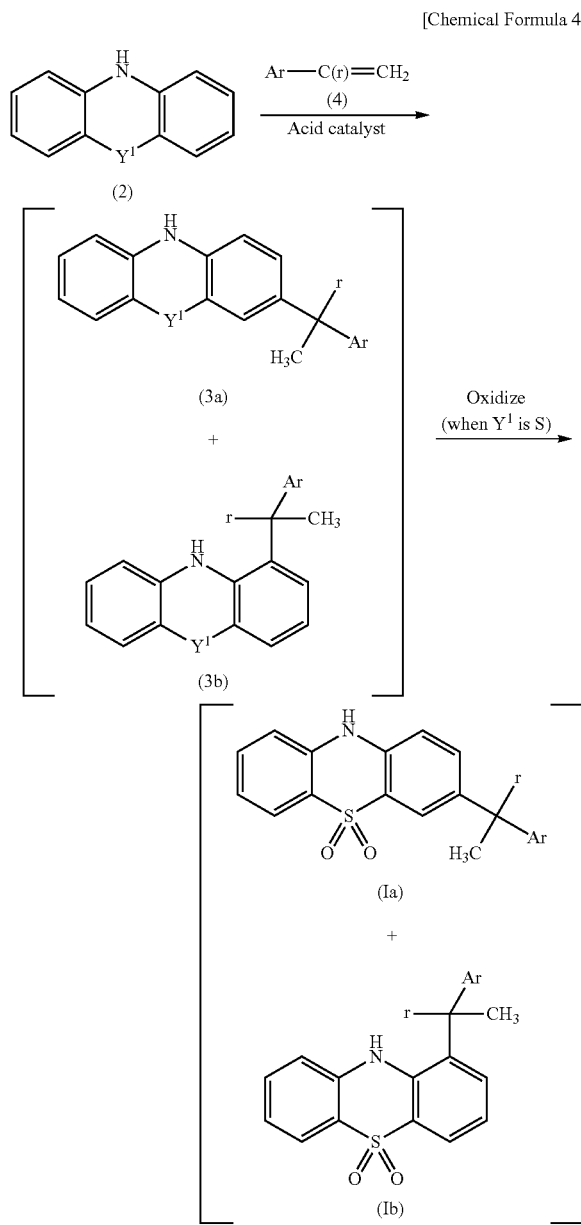

Further, in accordance with the above reaction formula, among the compounds which are expressed by the formula (I), a compound where Y is a chemical single bond can be obtained as a compound which is shown in the formula (3a) and/or (3b) by using a compound which is expressed by the formula (2) (carbazole where Y$^1$=chemical single bond) as a starting material and reacting the styrene compound which is expressed by the formula (4) in the presence of an acid catalyst.

Further, in accordance with the above reaction formula, among the compounds which are expressed by the formula (I), a compound where Y is —SO$_2$— can be obtained as a compound which is shown in the formula (Ia) and/or (Ib) by using a compound which is expressed by the formula (2) (phenothiazine where Y$^1$=S) as a starting material, reacting the styrene compound which is expressed by the formula (4) in the presence of an acid catalyst, and oxidizing the compound which is obtained by the reaction (compound which is shown in the formula (3a) and/or (3b)).

As a compound which is expressed by the formula (4) which is used for this reaction, styrene; an alkylated styrene such as 4-methylstyrene, α-methylstyrene, 4,α-dimethylstyrene, 2,4-dimethylstyrene, ethylstyrene, and p-t-butylstyrene; a halogenated styrene such as 2-chlorostyrene, and 2,4-dichlorostyrene; etc. may be mentioned.

The amount of use of the compound which is expressed by the formula (4) is 0.5 to 1.5 moles per 1 mole of the compound which is expressed by the formula (2).

As an acid catalyst which is used, sulfonic acids such as methanesulfonic acid, phenylsulfonic acid, and p-toluenesulfonic acid; inorganic acids such as hydrochloric acid, and sulfuric acid; etc. may be mentioned. The acid catalyst is usually charged at the time of start of the reaction, but may also be added in the middle of the reaction.

The amount of use of the acid catalyst is usually 0.005 to 0.5 mole per 1 mole of the compound which is expressed by the formula (2), preferably 0.01 to 0.3 mole, more preferably 0.02 to 0.1 mole.

This reaction can be performed in a suitable solvent. The solvent which is used is not particularly limited so long as being inert to the reaction, but, for example, aromatic hydrocarbon-based solvent such as benzene, toluene, and xylene; aliphatic hydrocarbon-based solvent such as n-pentane, n-hexane, n-octane, cyclopentane, and cyclohexane; halogenated hydrocarbon-based solvent such as 1,2-dichloroethane, and monochlorobenzene; etc. may be mentioned. These solvents may be used as single type alone or as two or more types combined. The amount of use of the solvent depends on the reaction scale etc., but is 1 ml to 100 ml per 1 g of the compound which is expressed by the formula (2).

Further, in the compound which is expressed by the formula (2), when Y$^1$=S, the oxidizing agent which is used for oxidation is not particularly limited. Acetic acid-hydrogen peroxide, organic peroxide such as m-chloroperbenzoic acid may be mentioned.

The amount of use of the oxidizing agent is 2 to 5 moles per 1 mole of the compound which is expressed by the formula (3a) or (3b).

Note that, when synthesizing a compound where Y is —SO—, the oxidizing agent should be used in an amount of 0.5 to 1.5 moles per 1 mole of the compound which is expressed by the formula (3a) or (3b).

Such an oxidation reaction can be performed in a suitable solvent. The solvent which is used is not particularly limited so long as being inert to the reaction, but, for example, aromatic hydrocarbon-based solvent such as benzene, toluene, and xylene; aliphatic hydrocarbon-based solvent such as n-pentane, n-hexane, n-octane, cyclopentane, and cyclohexane; halogenated hydrocarbon-based solvent such as dichloromethane, chloroform, 1,2-dichloroethane, and monochlorobenzene; acetic acid; etc. may be mentioned. These solvents may be used as single type alone or as two or more types combined.

The amount of use of the solvent depends in the reaction scale etc., but is 1 ml to 100 ml per 1 g of the compound which is expressed by the formula (3a) or (3b).

Furthermore, this reaction can also be performed continuously by adding to a reaction solution which includes a compound which is expressed by the formula (3a) and/or (3b) predetermined amounts of acetic acid and hydrogen peroxide.

[B. Method of Production (2) Using Reaction Method α]

The reaction formula of the method of production (2) which uses the reaction method α is shown below. Note that, in the following reaction formula, the case where, in the compound which is expressed by the formula (I), Y is a chemical single bond or —$SO_2$—, n and m are 1, and —$Z^a$—$R^a$ and —$Z^b$—$R^b$ are groups which are shown by the formula: —C($CH_3$)(r)—Ar (wherein, r indicates a hydrogen atom or alkyl group, and Ar indicates a substitutable phenyl group) is illustrated.

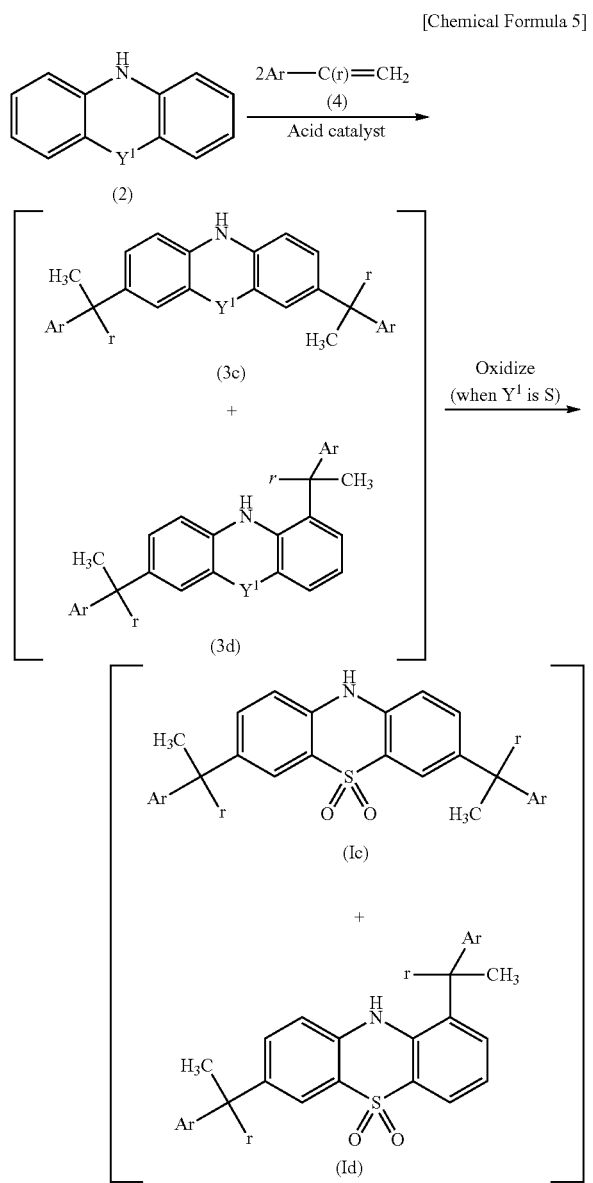

Further, in accordance with the above reaction formula, in the compound which is expressed by the formula (I), the compound where Y is a chemical single bond can be obtained as a compound of the formula (3c) and/or (3d) by using the compound which is expressed by the formula (2) (carbazole where $Y^1$=chemical single bond) as a starting material and reacting the styrene compound which is expressed by the formula (4) in the presence of an acid catalyst.

Further, in accordance with the above reaction formula, in the compound which is expressed by the formula (I), the compound where Y is —$SO_2$— can be obtained as a compound of the formula (Ic) and/or (Id) by using the compound which is expressed by the formula (2) (phenothiazine where $Y^1$=S) as a starting material, reacting the styrene compound which is expressed by the formula (4) in the presence of an acid catalyst, and oxidizing the compound which is obtained by the reaction (the compound which is shown by the formula (3c) and/or (3d))

Note that, in the above reaction, as the compound which is expressed by the formula (4), acid catalyst, solvent, and oxidizing agent, ones similar to the above-mentioned method of production (1) which uses the reaction method α can be used. Further, for the amounts of use of these, except for making the amount of use of the compound which is expressed by the formula (4) 2 to 3 moles per 1 mole of the compound which is expressed by the formula (2) and making the amount of use of the oxidizing agent 2 to 10 moles per 1 mole of the compound which is expressed by the formula (3c) or (3d), similar amounts to the above-mentioned method of production (1) which uses the reaction method α can be used.

[C. Method of Production Using Reaction Method β]

The reaction formula of the method of production which uses the reaction method β is shown below. Note that, in the following reaction formula, the case where, in the compound which is expressed by the formula (I), Y is a chemical single bond or —$SO_2$—, n or m are 0, and —$Z^a$—$R^a$ or —$Z^b$—$R^b$ are groups which are shown by the formula: —$SO_2$—Ar (wherein, Ar indicates a substitutable phenyl group) is illustrated.

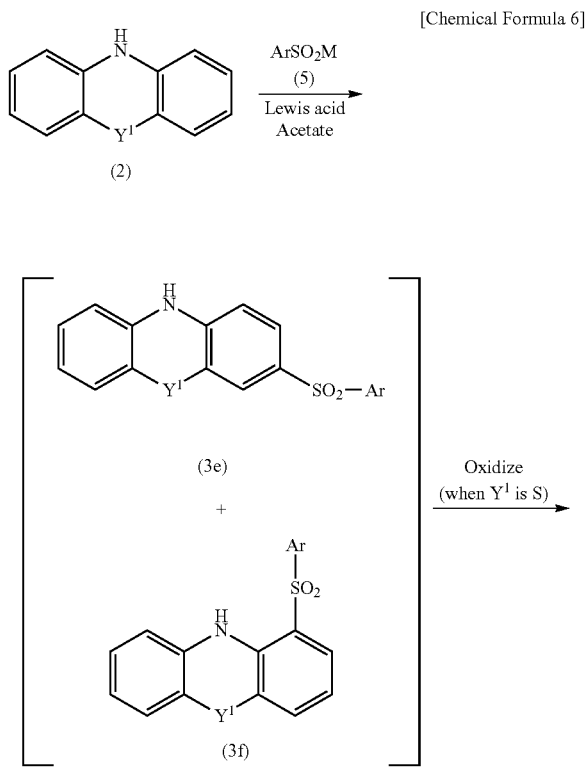

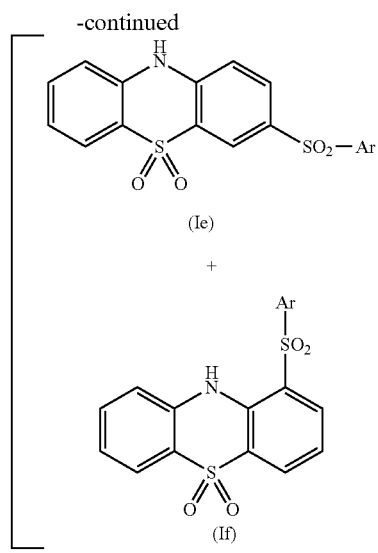

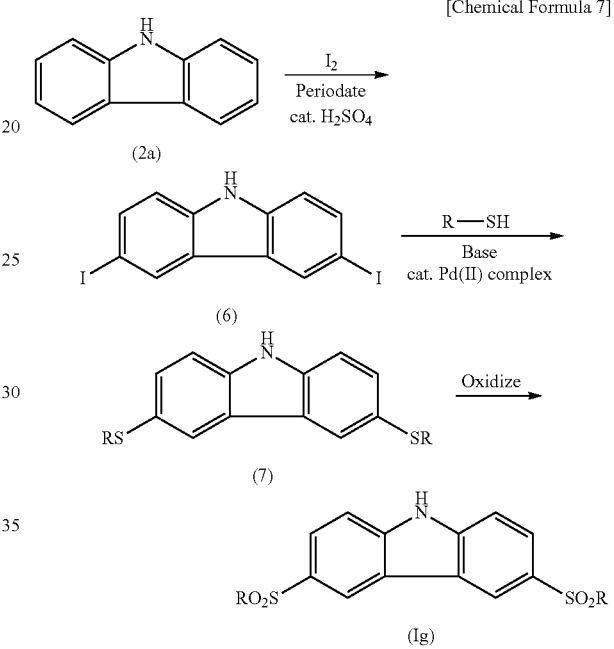

Further, in accordance with the above reaction formula, in the compound which is expressed by the formula (I), the compound where Y is a chemical single bond can be obtained as a compound of the formula (3e) and/or (3f) by using the compound which is expressed by the general formula (2) (carbazole where $Y^1$=chemical single bond) as a starting material and reacting the sulfinate which is expressed by the formula (5) in the presence of Lewis acid such as ferric chloride and acetate such as potassium acetate (M expressed alkali metal such as sodium).

Further, in accordance with the above reaction formula, in the compound which is expressed by the formula (I), the compound where Y is —$SO_2$— can be obtained as a compound of the formula (Ie) and/or (If) by using the compound which is expressed by the formula (2) (phenothiazine where $Y^1$=S) as a starting material, reacting the sulfinate which is expressed by the formula (5) in the presence of Lewis acid such as ferric chloride and acetate such as potassium acetate, and oxidizing the compound which is obtained by the reaction (compound which is shown by the formula (3e) and/or (3f)).

As the sulfinate which is expressed by the formula (5) which is used for the reaction, sodium phenylsulfinate, potassium phenylsulfinate, sodium p-toluenesulfinate, potassium p-toluenesulfinate, etc. may be mentioned.

The amount of use of the sulfinate which is expressed by the formula (5) is 0.5 to 1.5 moles per 1 mole of the compound which is expressed by the formula (2).

The amount of use of the Lewis acid is usually 5 to 10 moles per 1 mole of the compound which is expressed by the formula (2), while the amount of use of the acetate is usually 1 to 3 moles per 1 mole of the compound which is expressed by the formula (2).

The reaction can be performed in a suitable solvent. The solvent which is used is not particularly limited so long as being inert to the reaction, but, for example, alcohol-based solvent such as methyl alcohol, ethyl alcohol, propyl alcohol, and isopropyl alcohol may be mentioned.

The solvent which is used can be used as single type alone or as two or more types combined.

The amount of use of the solvent depends on the reaction scale etc., but is 1 ml to 100 ml per 1 g of the compound which is expressed by the formula (2).

Note that, in the compound which is expressed by the formula (2), when $Y^1$=S, the oxidation reaction can be performed in the same way as the above-mentioned method of production (1) which uses the reaction method α.

[D. Method of Production Using Reaction Method γ]

The reaction formula of the method of production which uses the reaction method γ is shown below. Note that, in the following reaction formula, the case where, in the compound which is expressed by the formula (I), Y is a chemical single bond, n and m are 1, and —$Z^a$—$R^b$ or —$Z^b$—$R^b$ are groups which are shown by the formula: —$SO_2$—R (wherein, R expresses a $C_1$ to $C_{30}$ organic group) is illustrated.

[Chemical Formula 7]

Further, in accordance with the above reaction formula, a compound which is expressed by the formula (2a) (carbazole) can be used as a starting material and iodine can be reacted in the presence of periodate and a catalytic amount of sulfuric acid to obtain diiodo which is expressed by the formula (6), then the obtained diiodo can be reacted with mercaptan which is expressed by the formula: R—SH (wherein, R indicates a $C_1$ to $C_{30}$ organic group) in the presence of a base and a catalytic amount of palladium (II) complex so as to obtain the compound which is expressed by the formula (7), then the obtained compound can be oxidized to obtain a compound which is expressed by the formula (Ig).

As the periodate which is used for the reaction for obtaining the diiodo which is shown in the formula (6), sodium periodate, potassium periodate, etc. may be mentioned.

The amount of use of the periodate is 0.1 mole to 1 mole per 1 mole of the compound which is expressed by the formula (2a).

The amount of use of iodine is 1 mole to 3 moles per 1 mole of the compound which is expressed by the formula (2a).

The reaction which obtains the diodo which is expressed by the formula (6) can be performed in a suitable solvent. The solvent which is used is not particularly limited so long as being inert to the reaction, but for example, alcohol-based solvent such as methyl alcohol, ethyl alcohol, propyl alcohol, and isopropyl alcohol may be mentioned.

The solvent which is used can be used as single type alone or as two or more types combined.

The amount of use of the solvent depends on the reaction scale etc., but is 1 ml to 100 ml per 1 g of the compound which is expressed by the formula (2a).

As a mercaptan which is used for the reaction for obtaining the compound which is expressed by the formula (7), thiophenol, p-toluenethiol, benzylmercaptan, α-methylbenzylmercaptan, α,α-dimethylmercaptan, t-butylmercaptan, etc. may be mentioned.

The amount of use of the mercaptan is 1 mole to 3 moles per 1 mole of the compound which is expressed by the formula (6).

As the base which is used for the reaction for obtaining the compound which is expressed by the formula (7), metal alkoxide such as sodium t-butoxide and potassium t-butoxide; organic base such as DBU (1,8-diazabicyclo[5.4.0]undeca-7-en), and DABCO (1,4-diazabicyclo[2.2.2]octane); etc. may be mentioned.

The amount of use of the base is usually 1 mole to 10 moles per 1 mole of compound which is expressed by the formula (6).

As a palladium (II) complex which is used for the reaction for obtaining the compound which is expressed by the formula (7), [1,1'-bis(diphenylphosphino) ferrocene]palladium (II) dichloride dichloromethane adduct etc. may be mentioned.

The reaction for obtaining the compound which is expressed by the formula (7) can be performed in a suitable solvent. The solvent which is used is not particularly limited so long as being inert to the reaction, but for example, aromatic hydrocarbon-based solvent such as benzene, toluene, and xylene; aliphatic hydrocarbon-based solvent such as n-pentane, n-hexane, n-octane, cyclopentane, and cyclohexane; halogenated hydrocarbon-based solvent such as dichloromethane, chloroform, 1,2-dichloroethane, and monochlorobenzene; etc. may be mentioned. These solvents can be used as single type alone or as two or more types combined.

The amount of use of the solvent depends on the reaction scale etc., but is 1 ml to 100 ml per 1 g of the compound which is expressed by the formula (6).

The oxidizing agent which is used for the oxidation reaction with the compound which is expressed by the formula (7) is not particularly limited, but organic peroxide such as acetic acid-hydrogen peroxide and m-chloroperbenzoic acid may be mentioned.

The amount of use of the oxidizing agent is 2 to 10 moles per 1 mole of the compound which is expressed by the formula (7).

Further, as the suitable solvent for such an oxidation reaction, a solvent similar to the one used in the oxidation reaction of the above-mentioned method of production (1) which uses the reaction method α may be used.

Furthermore, this reaction can be performed continuously by adding to a reaction solution which contains the compound which is expressed by the formula (7) predetermined amounts of acetic acid and hydrogen peroxide.

Each of the reactions of the above reaction method α, reaction method β, and reaction method γ proceeds smoothly in the temperature range from 0° C. up to the boiling point of the solvent which is used. The reaction time is usually several minutes to several hours.

Further, in each reaction of the reaction method α, reaction method β, and reaction method γ, after the end of the reaction, the usual post-treatment operations in organic synthetic chemicals are performed. If desired, the column chromatography, recrystallization method, distillation method, and other known separating and refining means can be applied to isolate the target substance.

The structure of the target substance can be identified by measurement of the NMR spectrum, IR spectrum, mass spectrum, etc. and by elementary analysis etc.

The condensed heterocyclic compound which was obtained in the above way can give high processing stability and heat resistance, and long life to a polymer or other organic material which is susceptible to oxidation, heat, or light induced breakdown.

The fact that the condensed heterocyclic compound of the present invention is superior in antiaging performance for organic materials can for example be confirmed as follows:

That is, a condensed heterocyclic compound of the present invention, an acrylic elastomer, carbon black, and stearic acid were kneaded in predetermined amounts, a cross-linking agent and a cross-linking accelerator in predetermined amounts are further added and kneaded to obtain a rubber composition, and the obtained rubber composition is formed into a sheet and cross-linked. Next, the obtained sheet is used as a test piece. This test piece is allowed to stand in a 190° C. environment for 504 hours in a heat degradation test. Before and after the test, the elongation is measured in accordance with JIS K6301. The rate of change of elongation which is calculated by the following calculation formula is usually −90 to −60(%) and is a value close to zero compared with the case of using a conventional antiaging agent. From this, it is learned that the condensed heterocyclic compound of the present invention has a superior stabilizing action (antiaging performance).

Rate of change (%)=[(elongation after test (%))−(elongation before test (%))]/(elongation before test (%))×100

The condensed heterocyclic compound of the present invention acts as an antiaging agent.

Specifically, the condensed heterocyclic compound of the present invention has the function of stabilizing an organic material against oxidation, heat, or light induced breakdown. In particular, the condensed heterocyclic compound of the present invention can suppress the natural oxidation and heat degradation of an organic material which is used in a high temperature so as to improve the heat resistance and processing stability of the organic material and increase the lifetime.

When using the condensed heterocyclic compound of the present invention as a stabilizing agent of an organic material, the amount of the condensed heterocyclic compound of the present invention is, with respect to 100 g of the organic material, 0.5 to 100 mmoles, preferably 1 to 50 moles, particularly preferably 1 to 30 moles. If the amount of the condensed heterocyclic compound of the present invention is smaller than 0.5 mmole, the effect as a stabilizing agent is not exhibited. If greater than 100 mmoles, no improvement in effect as a stabilizing agent is seen, contrariwise, there is a possibility of bleedout or discoloration of the molded product. This is not preferable.

Further, the condensed heterocyclic compound of the present invention may be used alone or may be used as two or more types combined. Furthermore, it can be used combined with a conventionally used stabilizing agent in a range not detracting from the effect of the invention.

2) Composition which Contains Organic Material and Condensed Heterocyclic Compound A second aspect of the present invention is a composition which contains an ingredient (a) of an organic material and an ingredient (b) of a condensed heterocyclic compound of the present invention.

The organic material of the ingredient (a) which is used in the present invention is not particularly limited. It may be a natural organic material or a synthetic organic material. Among these, as the organic material of the ingredient (a), due to the large effect of addition of the condensed heterocyclic compound of the present invention, a synthetic rubber, polyolefin, polystyrene-based resin, polyester, polycarbonate, polyamide, or other synthetic polymer which is used for applications where heat resistance is demanded are preferable, while a synthetic rubber is more preferable.

The synthetic rubber which can form the composition of the present invention is not particularly limited, but for example, rubber in which conjugated diene units are contained such as isoprene rubber, butadiene rubber, butyl rubber, chloroprene rubber, styrene-butadiene copolymer rubber, acrylonitrile-butadiene copolymer rubber (nitrile rubber), styrene-butadiene-isoprene copolymer rubber, butadiene-isoprene copolymer rubber, and acrylonitrile-styrene-butadiene copolymer rubber; Acrylic rubber, hydrin rubber, ethylenepropylene rubber; etc. may be mentioned. These synthetic rubbers may also have hydroxyl groups, carboxyl groups, alkoxysilyl groups, amino groups, epoxy groups, etc. Further, these rubbers may also be hydrogenated. For example, Hydrogenated acrylonitrile-butadiene copolymer rubber (hydrogenated nitrile rubber) may be mentioned. These synthetic rubbers may be used alone or may be used as two or more types combined. Among these as well, in particular, application to an acrylic rubber or hydrogenated nitrile rubber from which a high heat resistance is sought is preferable from the viewpoint of the effect of improvement of the heat resistance, while application to acrylic rubber is more preferable.

(Acrylic Rubber)

The acrylic rubber which can be used in the present invention is rubber which has (meth)acrylic acid ester monomer units in 50 to 100 wt % and cross-linkable monomer units in 10 to 0 wt % and, units of other monomers which are copolymerizable with the monomers which form these monomer units in 50 to 0 wt % added in accordance with need. By adjusting the ratios of the monomer units which form the acrylic rubber, it is possible to adjust the rubber physical properties. Further, in the present invention, "(meth)acryl" indicates acryl and/or methacryl.

An acrylic rubber is known as a rubber which is superior in oil resistance, in particular oil resistance under a high temperature, and which is excellent in heat resistance. Demand has been increasing for it for automobile-use hoses, oil seals, and O-rings and for conveyor belts built into equipment and facilities.

The (meth)acrylic acid ester monomer which forms the (meth)acrylic acid ester monomer units as the main ingredient of an acrylic rubber, is not particularly limited, but, for example, as preferable ones, a (meth)acrylic acid alkyl ester monomer, (meth)acrylic acid alkoxyalkyl ester monomer, etc. may be mentioned.

The (meth)acrylic acid alkyl ester monomer is not particularly limited, but esters of $C_1$ to $C_8$ alkanols and (meth)acrylic acid are preferable, specifically, methyl (meth)acrylate, ethyl (meth)acrylate, n-propyl (meth)acrylate, n-butyl (meth)acrylate, isopropyl (meth)acrylate, isobutyl (meth)acrylate, n-hexyl (meth)acrylate, 2-ethylhexyl (meth)acrylate, cyclohexyl (meth)acrylate, etc. may be mentioned. Among these as well, ethyl (meth)acrylate and n-butyl (meth)acrylate are preferable, while ethyl acrylate and n-butyl acrylate are more preferable. These may be used as single type alone or two or more types combined.

The (meth)acrylic acid alkoxyalkyl ester monomer is not particularly limited, but esters of $C_2$ to $C_8$ alkoxyalkyl alcohols and (meth)acrylic acid are preferable, specifically, methoxymethyl (meth)acrylate, ethoxymethyl (meth)acrylate, 2-methoxyethyl (meth)acrylate, 2-ethoxyethyl (meth)acrylate 2-propoxyethyl (meth)acrylate, 2-butoxyethyl (meth) acrylate, 3-methoxypropyl (meth)acrylate, 4-methoxybutyl (meth)acrylate, etc. may be mentioned. Among these as well, 2-ethoxyethyl (meth)acrylate and 2-methoxyethyl (meth) acrylate are preferable, while 2-ethoxyethyl acrylate and 2-methoxyethyl acrylate are particularly preferable. These may be used as single type alone or two or more types combined.

In the acrylic rubber, the content of the (meth)acrylic acid ester monomer units is 50 to 100 wt %, preferably 60 to 99.5 wt %, more preferably 70 to 99.5 wt %. If the content of the (meth)acrylic acid ester monomer units is too small, the obtained cross-linked rubber is liable to fall in weather resistance, heat resistance, and oil resistance.

The (meth)acrylic acid ester monomer units are preferably comprised of (meth)acrylic acid alkyl ester monomer units in 30 to 100 wt % and (meth)acrylic acid alkoxyalkyl ester monomer units in 70 to 0 wt %.

The cross-linkable monomer which forms the cross-linkable monomer units is not particularly limited, but an $\alpha,\beta$-ethylenically unsaturated carboxylic acid monomer; a monomer which has halogen atom or epoxy group; a diene monomer; etc. may be mentioned.

These cross-linkable monomers can be used as single type alone or as two or more types combined. In the acrylic rubber, the content of the cross-linkable monomer units is 0 to 10 wt %, preferably 0.5 to 7 wt %, more preferably 0.5 to 5 wt %. If the content of these cross-linkable monomer units is too great, the obtained cross-linked rubber product may fall in elongation or increase in the rate of compression set.

Other monomers which is copolymerizable with the above monomers are not particularly limited, but, for example, an aromatic vinyl monomer, $\alpha,\beta$-ethylenically unsaturated nitrile monomer, a monomer which has two or more acryloyloxy groups, olefin-based monomer, vinyl ether compound, etc. may be mentioned.

These copolymerizable other monomers may be used as a single type alone or two or more types combined. In the acrylic rubber, the content of the units of the other monomer is 0 to 50 wt %, preferably 0 to 39.5 wt %, more preferably 0 to 29.5 wt %.

The acrylic rubber which is used in the present invention can be obtained by polymerizing the above monomers. As the type of the polymerization reaction, any of the emulsion polymerization method, suspension polymerization method, bulk polymerization method, and solution polymerization method can be used, but from the viewpoint of the ease of control of the polymerization reaction and other factors, use of the emulsion polymerization method under ordinary pressure, which is generally used as the method of production of conventional known acrylic rubber, is preferable.

The emulsion polymerization may be either of the batch type, semi batch type, or continuous type. The polymerization is usually performed at 0 to 70° C., preferably 5 to 50° C. in temperature range.

The thus produced acrylic rubber which is used in the present invention has a Mooney viscosity ($ML_{1+4}$, 100° C.) (Polymer Mooney) of preferably 10 to 80, more preferably 20 to 70, furthermore preferably 25 to 60.

(Hydrogenated Nitrile Rubber)

The hydrogenated nitrile rubber which can be used in the present invention is a nitrile rubber which has $\alpha,\beta$-ethylenically unsaturated nitrile monomer units and conjugated diene monomer units, and monomer units which are derived from other monomer which is copolymerizable with the monomers which form the monomer units added in accordance with need and which is hydrogenated (hydrogenation reaction). Hydrogenated nitrile rubber, which is obtained by hydrogenating at least part of the carbon-carbon unsaturated bonds which the conjugated diene monomer units have, so is known as rubber which is superior in heat resistance, sour gasoline resistance, and ozone resistance and is known as a high performance material at a high temperature in applications such as seals, hoses and packing.

The α,β-ethylenically unsaturated nitrile monomer which forms the α,β-ethylenically unsaturated nitrile monomer units is not particularly limited, but, for example, acrylonitrile, methacrylonitrile, α-chloroacrylonitrile, etc. may be mentioned. Among these as well, acrylonitrile is preferable. These may be used as single type alone, but may also be used jointly as several types. The content of the α,β-ethylenically unsaturated nitrile monomer units in the hydrogenated nitrile rubber is preferably 10 to 60 wt %, more preferably 12 to 55 wt %, furthermore preferably 15 to 50 wt %. Depending on the content of the α,β-ethylenically unsaturated nitrile monomer units, the oil resistance, cold resistance, heat resistance, sour gasoline resistance, ozone resistance, and other properties differ, it can be widely selected in accordance with the applications.

The conjugated diene monomer which forms the conjugated diene monomer units is not particularly limited, but for example, 1,3-butadiene, isoprene, 2,3-dimethyl-1,3-butadiene, 1,3-pentadene, etc. may be mentioned, while 1,3-butadiene is preferable. The content of the conjugated diene monomer units in the hydrogenated nitrile rubber is preferably 40 to 90 wt %, more preferably 45 to 88 wt %, furthermore preferably 50 to 85 wt %.

Further, the other monomer described above is not particularly limited, but a diene monomer other than a conjugated diene monomer, α-olefin, α,β-ethylenically unsaturated carboxylic acid ester, aromatic vinyl-based monomer, fluorine-containing vinyl-based monomer, α,β-ethylenically unsaturated monocarboxylic acid, α,β-ethylenically unsaturated dicarboxylic acid, anhydride of an α,β-ethylenically unsaturated dicarboxylic acid, copolymerizable antiaging agent, etc. may be illustrated. These copolymerizable other monomers may be jointly used in a plurality of types.

The method of production of the nitrile rubber is not particularly limited. In general, the method of copolymerizing the α,β-ethylenically unsaturated nitrile monomer, conjugated diene monomer, and other monomer, which is added in accordance with need, copolymerizable with these is simple and preferable. As the polymerization method, any of the known emulsion polymerization method, suspension polymerization method, bulk polymerization method, and solution polymerization method may be employed, but due to the ease of control of the polymerization reaction, the emulsion polymerization method is preferable.

The nitrile rubber which is produced is hydrogenated to make it a hydrogenated nitrile rubber whereby the heat resistance, sour gasoline resistance, and ozone resistance are further improved. The method of performing the hydrogenation (hydrogenation reaction) is not particularly limited. A known method can be employed.

The hydrogenated nitrile rubber is also not particularly limited in iodine value (measured in accordance with JIS K6235). When performing a hydrogenation reaction, it is preferably 120 or less, more preferably 60 or less, furthermore preferably 30 or less. If the iodine value is too high, the heat resistance becomes poor.

The hydrogenated nitrile rubber has a Mooney viscosity ($ML_{1+4}$, 100° C.) (Polymer Mooney) of preferably 15 to 200, more preferably 30 to 150, particularly preferably 45 to 120.

If the hydrogenated nitrile rubber is too low in Mooney viscosity, the cross-linked rubber is liable to fall in mechanical properties, while conversely if it is too high in Mooney viscosity, the workability may fall.

The composition of the present invention may contain, in addition to the ingredient (a) and the ingredient (b), other additives.

As the other additives, additives which are usually used in the field of synthetic polymer materials may be mentioned. For example, reinforcing fillers such as carbon black, and silica; nonreinforcing fillers such as calcium carbonate, and clay; photo stabilizers; scorch retarders; plasticizers; processing aids; slip agents; tackifiers; lubricants; flame retardants; antifungal agents; antistatic agents; coloring agents; silane coupling agents; cross-linking agents; cross-linking accelerators; cross-linking retardants; etc. may be mentioned.

The amounts of these additives are not particularly limited so long as in ranges not detracting from the object and effects of the present invention. Amounts in accordance with the purpose of compounding can be suitably blended.

The composition of the present invention can be prepared by mixing and kneading the ingredient (a), ingredient (b), and other additives as desired in predetermined amounts by a Bambury mixer, kneader, etc., next, further kneading them by a kneading roll.

The order of blending in the ingredients is not particularly limited, but it is preferable to first fully mix the ingredients which are resistant to reaction and decomposition by heat, then mix in the ingredients which easily react or decompose due to heat such as the cross-linking agent etc. in a short time at a temperature at which the reaction or decomposition will not occur.

According to the composition of the present invention, it is possible to impart high processing stability and heat resistance, and long life to a polymer or other organic material which is susceptible to oxidation, heat, or light induced breakdown.

EXAMPLES

Below, examples, manufacturing examples, and comparative examples will be give to explain the present invention more specifically, but the present invention is not limited to these examples.

Example 1

Synthesis of Compound 1

The following method was followed to synthesize the compound 1 of the following formula (X).

[Chemical Formula 8]

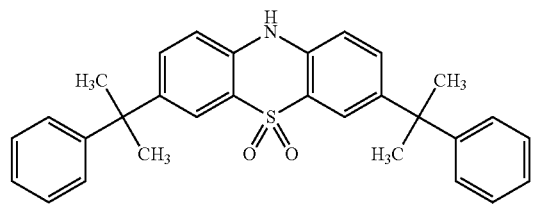

(X)

That is, first, a three-necked reactor which was equipped with a thermometer was charged with, in a nitrogen stream, phenothiazine 50.0 g (250.92 mmol), then this was made to dissolve in toluene 200 ml. Next, to this solution, α-methylstyrene 59.31 g (501.83 mmol) and p-toluenesulfonic acid monohydrate 1.19 g (6.27 mmol) were added and the result made to react at 80° C. for 1 hour. After that, the reaction solution was returned to room temperature, then acetic acid 48 ml and 30% hydrogen peroxide solution 85.34 g (752.7 mmol) were added and the result further made to react at 80° C. for 2 hours. The reaction solution was returned to room temperature, then was charged into methanol 630 ml. The precipitated crystal was filtered and was rinsed by 320 ml of methanol to thereby obtain a white crystal compound 1 in 85.7 g for a yield of 73%. The structure was identified by $^1$H-NMR.

$^1$H-NMR (500 MHz, DMSO-d6, TMS, δppm): 1.67 (s, 12H), 7.15-7.32 (m, 12H), 7.43 (dd, 2H, J=9.0, 2.0 Hz), 7.68 (d, 2H, J=1.5 Hz), 10.84 (s, 1H).

Example 2

Synthesis of Compound 2

The following method was followed to synthesize the compound 2 which is shown in the following formula (XI).

[Chemical Formula 9]

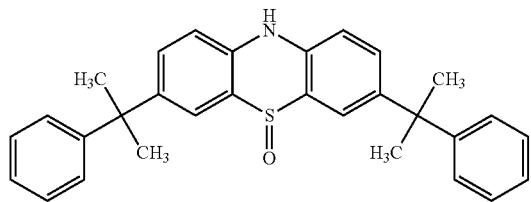

(XI)

That is, first, a three-necked reactor which was equipped with a thermometer was charged, in a nitrogen stream, with phenothiazine 30.0 g (150.55 mmol), then this was made to dissolve in toluene 175 ml. Next, to this solution, α-methylstyrene 35.58 g (301.10 mmol) and p-toluenesulfonic acid monohydrate 0.72 g (3.76 mmol) were added and the result reacted at 80° C. for 1 hour. The reaction solution was returned to room temperature, then acetic acid 60 ml was added, 30%; hydrogen peroxide solution 17.07 g (150.55 mmol) was slowly added dropwise over 30 minutes, and the result was further reacted at room temperature for 2 hours. After that, the reaction solution was charged with methanol 760 ml and the precipitated crystal was filtered, then rinsed by 380 ml of methanol to thereby obtain a white crystal compound 2 in 55.5 g for a yield of 82%. The structure was identified by $^1$H-NMR.

$^1$H-NMR (500 MHz, DMSO-d6, TMS, δppm): δ 1.68 (s, 6H), 1.70 (s, 6H), 7.15-7.32 (m, 12H), 7.38 (dd, 2H, J=9.0, 2.0 Hz), 7.70 (d, 2H, J=1.5 Hz), 10.85 (s, 1H).

Example 3

Synthesis of Compound 3

The following method was followed to synthesize the compound 3 of the following formula (XII). Note that, when synthesizing the compound 3, this was synthesized by first obtaining the intermediate A which is shown by the following formula (XIII) and oxidizing the obtained intermediate A.

[Chemical Formula 10]

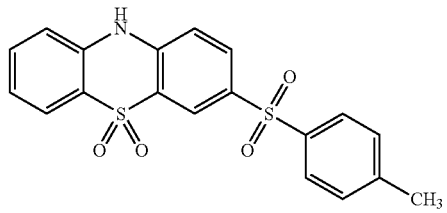

(XII)

[Chemical Formula 11]

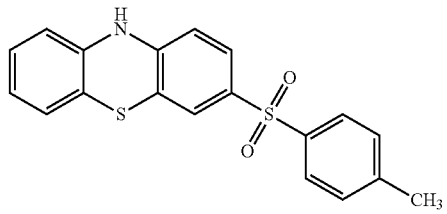

(XIII)

First, the following method was used to produce the intermediate A. That is, a two-necked reactor was charged with phenothiazine 13.34 g (66.94 mmol) and sodium p-toluenesulfinate 13.12 g (73.63 mmol), then these were made to dissolve in methanol 500 ml. To this solution, potassium acetate 13.14 g (133.9 mmol) and iron trichloride 86.87 g (538.6 mmol) were added and the total volume was made to react under refluxing conditions for 3 hours. After that, the reaction solution was concentrated by an evaporator down to 50 ml or so, then 0.2N hydrochloric acid aqueous solution 300 ml and saturated sodium chloride solution 500 ml were added and the result was extracted by ethyl acetate 800 ml. The extracted organic phase was further washed by 0.1N sodium hydroxide aqueous solution 200 ml, dried over anhydrous sodium sulfate, then concentrated by a rotary evaporator. The concentrate was made to dissolve in tetrahydrofuran (THF) and methanol was added to cause it to reprecipitate to thereby obtain a white crystal intermediate A in 12.07 g (yield 510). The structure of the obtained intermediate A was identified by $^1$H-NMR.

$^1$H-NMR (500 MHz, DMSO-d6, δppm): 2.36 (s, 3H), 6.66 (d, 1H, J=7.5 Hz), 6.72 (d, 1H, J=8.5 Hz), 6.80 (t, 1H, J=7.5 Hz), 6.90 (d, 1H, J=7.5 Hz), 7.00 (t, 1H, J=7.5 Hz), 7.37 (d, 1H, J=1.5 Hz), 7.39 (d, 2H, J=8.0 Hz), 7.48 (dd, 1H, J=8.5, 1.5 Hz), 7.77 (d, 2H, J=8.0 Hz), 9.17 (s, 1H).

Next, the obtained intermediate A was used in accordance with the following method to obtain the compound 3. That is, first, a two-necked reactor was charged with the intermediate A 11.0 g (31.12 mmol) which was obtained above, then this was made to dissolve in THF 800 ml. Next, to this solution, acetic acid 600 ml and 30% hydrogen peroxide solution 21.17 g (186.7 mmol) were added and the total volume was made to react at 80° C. for 2 hours. The reaction solution was returned to room temperature, then was charged into distilled water 4 liters. The precipitated crystal was filtered. The obtained crystal was made to dissolve in THF and n-hexane was added to cause it to reprecipitate to thereby obtain a white crystal compound 3 in 11.05 g for a yield of 93%. The structure of the obtained compound 3 was identified by $^1$H-NMR.

$^1$H-NMR (500 MHz, DMSO-d6, TMS, δppm): 2.37 (s, 3H), 7.36 (t, 1H, J=7.5 Hz), 7.41 (d, 1H, J=8.5 Hz), 7.44 (d, 2H, J=8.0 Hz), 7.51 (d, 1H, J=9.0 Hz), 7.73 (t, 1H, J=8.0 Hz), 7.84 (d, 2H, J=8.0 Hz), 7.99 (d, 1H, J=8.0 Hz), 8.12 (dd, 1H, J=9.0, 1.5 Hz), 8.34 (d, 1H, J=1.5 Hz), 11.53 (s, 1H).

Example 4

Synthesis of Compound 4

The following method was followed to synthesize the compound 4 of the following formula (XIV). Note that, when synthesizing the compound 4, this was synthesized by first obtaining the intermediate B which is shown by the following formula (XV), next obtaining the intermediate C which is shown by the following formula (XVI) from the obtained intermediate B, and finally oxidizing the obtained intermediate C.

[Chemical Formula 12]

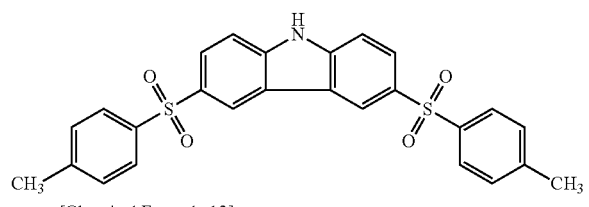

(XIV)

[Chemical Formula 13]

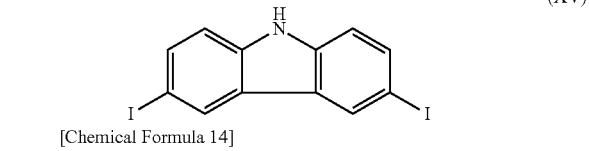

(XV)

[Chemical Formula 14]

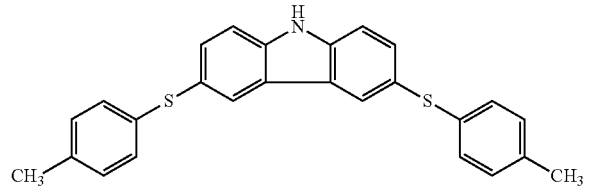

(XVI)

First, the following method was used to produce the intermediate B. That is, a two-necked reactor was charged with carbazole 25.0 g (149.5 mmol) and iodine 30.36 g (239.2 mmol), then these were made to dissolve in ethanol 600 ml. Next, to this solution, sodium periodate 12.8 g (59.80 mmol) was added. Further, concentrated sulfuric acid 1 g was slowly added dropwise, then the total volume was made to react at 65° C. for 3 hours. After that, the reaction solution was returned to room temperature, was concentrated by a rotary evaporator down to 150 ml or so, then the concentrated solution was charged with distilled water 500 ml and saturated sodium chloride solution 300 ml and the result was extracted by chloroform 1000 ml. The organic layer was made to dry over anhydrous sodium sulfate, was concentrated by a rotary evaporator, then the concentrate was charged with n-hexane to recrystallize it and thereby obtain the intermediate B in 34.4 g for a yield of 55%. The structure of the obtained intermediate B was identified by $^1$H-NMR.

$^1$H-NMR (500 MHz, DMSO-d6, TMS, δppm): 7.35 (d, 2H, J=8.5 Hz), 7.66 (dd, 2H, J=8.5, 1.5 Hz), 8.57 (d, 2H, J=1.5 Hz), 11.54 (s, 1H).

Next, the obtained intermediate B was used in accordance with the following method to obtain the intermediate C. That is, first, a two-necked reactor was charged with, in a nitrogen stream, the intermediate B 15.0 g (35.80 mmol) which was obtained above and p-toluenethiol 9.34 g (75.18 mmol), then these were made to dissolve in toluene 350 ml. Next, to this solution, sodium tert-butoxide 17.20 g (179.0 mmol), [1,1'-bis(diphenylphosphino)ferrocene]palladium (II) dichloride dichloromethane adduct 0.73 g (0.895 mmol) were added and the total volume was made to react at 80° C. for 4 hours. After that, the reaction solution was returned to room temperature, distilled water 1000 ml and saturated sodium chloride solution 500 ml were added, and the result was extracted by ethyl acetate 500 ml. The organic layer was made to dry over anhydrous sodium sulfate, was concentrated by a rotary evaporator, then was purified by silica gel column chromatography (n-hexane: tetrahydrofuran=3:1 (volume ratio)) to thereby obtain the intermediate C in 9.14 g for a yield of 62%. The structure of the obtained intermediate C was identified by $^1$H-NMR.

$^1$H-NMR (500 MHz, CDCl3, TMS, δppm): 2.29 (s, 6H) 7.05 (d, 4H, J=8.0 Hz), 7.15 (d, 4H, J=8.0 Hz), 7.37 (d, 2H, J=8.5 Hz), 7.51 (dd, 2H, J=8.5, 1.5 Hz), 8.12 (d, 2H, J=1.5 Hz), 8.18 (s, 1H).

Next, the obtained intermediate C was used in accordance with the following method to obtain the compound 4. That is, first, a two-necked reactor was charged with the intermediate C 8.00 g (19.44 mmol) which was obtained above, then this was made to dissolve in THF 160 ml. To this solution, acetic acid 240 ml and 30% hydrogen peroxide solution 13.22 g (116.6 mmol) were added, and the total volume was made to react at 80° C. for 10 hours. The reaction solution was returned to room temperature, then was charged into distilled water 1.5 liters. The precipitated crystal was filtered, made to dissolve in THF, and reprecipitated by adding methanol to thereby obtain a white crystal compound 4 in 8.04 g for a yield of 87%. The structure of the obtained compound 4 was identified by $^1$H-NMR.

$^1$H-NMR (500 MHz, DMSO-d6, TMS, δppm): 2.34 (s, 6H), 7.40 (d, 4H, J=8.0 Hz), 7.71 (d, 2H, J=8.5 Hz), 7.89 (d, 4H, J=8.0 Hz), 7.99 (dd, 2H, J=8.5, 1.5 Hz), 9.11 (d, 2H, J=1.5 Hz), 12.33 (s, 1H).

Manufacturing Example 1

Synthesis of Compound 5

The following method was followed to synthesize the compound 5 which is shown in the following formula (XVII).

[Chemical Formula 15]

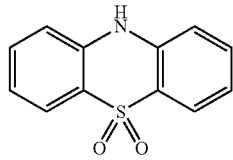

(XVII)

That is, first, a two-necked reactor was charged with phenothiazine 20.0 g (100.4 mmol), then this was made to dissolve in acetic acid 200 ml. Next, to this solution, 30% hydrogen peroxide solution 34.13 g (301.1 mmol) was added, and the total volume was made to react at 80° C. for 2 hours. After that, the reaction solution was returned to room temperature, charged with distilled water 100 ml, and further was stirred for 1 hour. The precipitated crystal was filtered and made to dry to thereby obtain an orange colored crystal of the compound 5 in 20.5 g for a yield of 88%. The structure of the obtained compound 5 was identified by $^1$H-NMR.

$^1$H-NMR (500 MHz, DMSO-d6, TMS, δppm): 7.25 (t, 2H, J=8.0 Hz), 7.35 (d, 2H, J=8.0 Hz), 7.66 (t, 2H, J=8.0 Hz), 7.93 (d, 2H, J=8.0 Hz), 10.94 (s, 1H).

Examples 5 to 10

Preparation of Rubber Compositions

The compounds 1 to 4 which were produced in Examples 1 to 4 (antiaging agents) were used in the amounts described in the following Table 1 and kneaded together with an acrylic elastomer (made by Zeon Corporation, Nipol AR22) 100 g, carbon black (made by Tokai Carbon, Seast SO) 60 g, and stearic acid 2 g using a Bambury mixer at 50° C., then the obtained mixtures were charged with predetermined amounts of a cross-linking agent and cross-linking accelerator and the results kneaded by open rolls to prepare the rubber compositions of Examples 5 to 10.

Note that, as the cross-linking agent, hexamethylenediamine carbamate (made by Dupont Dow Elastomer Japan, Diak No. 1) (below, referred to as the "cross-linking agent A") was used.

Further, as the cross-linking accelerator, 1,3-di-o-tolylguanidine (made by Ouchi Shinko Chemical Industrial, Nocceler DT) (below, referred to as the "cross-linking accelerator A") was used.

TABLE 1

Table 1

| | Ex. 5 | Ex. 6 | Ex. 7 | Ex. 8 | Ex. 9 | Ex. 10 |
|---|---|---|---|---|---|---|
| Antiaging agent | Compound 1 | Compound 1 | Compound 1 | Compound 2 | Compound 3 | Compound 4 |
| Amount added (g) | 1.58 | 4.12 | 5.96 | 5.75 | 4.91 | 6.05 |
| moles (mmol) | 3.39 | 8.81 | 12.73 | 12.73 | 12.73 | 12.73 |

Comparative Examples 1 to 10

Preparation of Rubber Compositions

The antiaging agents which are shown in the following Table 2 were used in the amounts which are described in the following Table 3 and kneaded with an acrylic elastomer (made by Zeon Corporation, Nipol AR22) 100 g, carbon black (made by Tokai Carbon, Seast SO) 60 g, and stearic acid 2 g using a Bambury mixer at 50° C., then the obtained mixtures were charged with predetermined amounts of the cross-linking agent A and cross-linking accelerator A and kneaded by open rolls to prepare the rubber compositions of Comparative Examples 1 to 10.

TABLE 2

Table 2

| Antiaging agent | Compound (manufacturer name, product name) |
|---|---|
| A | Diphenylamine |
| B | 4,4'-di-t-butyldiphenylamine (made by Seiko Chemical, Stearer STAR) |
| C | 4,4'-bis(α-methylbenzyl)diphenylamine and 4-(α-methylbenzyl)diphenylamine in mixture (made by Seiko Chemical, Nonflex LAS-P) |
| D | N,N'-di-2-naphthyl-p-phenylenediamine (made by Ouchi Shinko Chemical Industrial, Nocrac White) |
| E | N,N'-diphenyl-p-phenylenediamine (made by Ouchi Shinko Chemical Industrial, Nocrac DP) |
| F | 4,4'-di-n-octyldiphenylamine (made by Ouchi Shinko Chemical Industrial, Nocrac AD-F) |
| G | Carbazole |
| H | Compound 5 |
| I | 4,4'-bis(α,α-dimethylbenzyl)diphenylamine (made by Chemtura, Nauguard 445) |

TABLE 3

Table 3

| | Comp. Ex. 1 | Comp. Ex. 2 | Comp. Ex. 3 | Comp. Ex. 4 | Comp. Ex. 5 |
|---|---|---|---|---|---|
| Antiaging agent | None | Antiaging agent A | Antiaging agent B | Antiaging agent C | Antiaging agent D |
| Amount added (g) | — | 0.84 | 1.12 | 1.94 | 1.78 |
| moles (mmol) | — | 4.93 | 4.93 | 4.93 | 4.93 |

| | Comp. Ex. 6 | Comp. Ex. 7 | Comp. Ex. 8 | Comp. Ex. 9 | Comp. Ex. 10 |
|---|---|---|---|---|---|
| Antiaging agent | Antiaging agent E | Antiaging agent F | Antiaging agent G | Antiaging agent H | Antiaging agent I |
| Amount added (g) | 1.28 | 1.94 | 2.13 | 2.94 | 6.05 |
| moles (mmol) | 4.93 | 4.93 | 12.73 | 12.73 | 12.73 |

The rubber compositions which were obtained in Examples 5 to 10 and Comparative Examples 1 to 10 were molded by a press and cross-linked at 170° C. for 20 minutes to prepare 15 cm×15 cm×2 mm sheets. Further, these sheets were heated at 170° C. for 4 hours to cause secondary cross-linking. The sheets were used as test pieces.

<Test for Evaluation of Heat Resistance>

The test pieces which were prepared in Examples 5 to 10 and Comparative Examples 1 to 10 were measured for elongation in accordance with JIS K6301 before and after a heat degradation test where they were allowed to stand in an environment of 190° C. for 504 hours. The following calculation formula was used to calculate the rates of change. The closer the rate of change to zero, the higher the heat resistance is judged and the more preferable the result.

Rate of change (%)=[(elongation after test (%))−(elongation before test (%))]/(elongation before test (%))]×100

The results of evaluation of the heat resistance are summarized in Table 4. Note that, in Table 4, the elongation at break before the heat degradation test (%) and the rate of change of the elongation at break before and after the heat degradation test (%) are shown.

TABLE 4

| | Elongation at break (%) | Rate of change in elongation after 504 hours (%) |
|---|---|---|
| Example 5 | 260 | −65 |
| Example 6 | 260 | −63 |
| Example 7 | 270 | −62 |
| Example 8 | 270 | −63 |
| Example 9 | 240 | −75 |
| Example 10 | 230 | −78 |
| Comparative Example 1 | 250 | −93 |
| Comparative Example 2 | 260 | −89 |
| Comparative Example 3 | 260 | −88 |
| Comparative Example 4 | 250 | −89 |
| Comparative Example 5 | 260 | −87 |
| Comparative Example 6 | 270 | −87 |
| Comparative Example 7 | 260 | −86 |
| Comparative Example 8 | 235 | −90 |
| Comparative Example 9 | 240 | −89 |
| Comparative Example 10 | 280 | −84 |

From Table 4, the rubber compositions of Examples 5 to 10 which contain the compounds 1 to 4 of Examples 1 to 4 (condensed heterocyclic compounds of the present invention) had rates of change of elongation before and after heat degradation tests of −78% to −62% and values close to zero compared with a rubber composition not containing any antiaging agent (Comparative Example 1) and rubber compositions containing conventional antiaging agents (Comparative Examples 2 to 10).

Accordingly, it is learned that the compounds 1 to 4 of Examples 1 to 4 (condensed heterocyclic compounds of present invention) have excellent stabilizing actions on acrylic elastomers compared with conventional antiaging agents (antiaging performance).

The invention claimed is:

1. A condensed heterocyclic compound which is shown in the following formula (I),

[Chemical Formula 16]

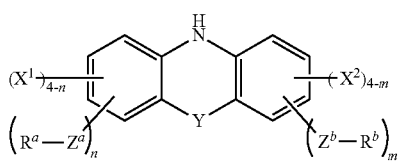

(I)

where, in the formula, Y represents —S(O)—, —SO$_2$—, —Z$^a$—R$^a$ and —Z$^b$—R$^b$ independently represent α-methylbenzyl groups, α,α-dimethylbenzyl groups, phenylsulfonyl groups, or 4-methylphenylsulfonyl groups, X$^1$ and X$^2$ represent hydrogen atoms, n and m independently represent integers of 0 to 2, however, at least one of n and m is not 0, and when n and/or m is 2, two of R$^a$ and two of R$^b$ may be the same as each other or may be different.

2. The condensed heterocyclic compound as set forth in claim 1, which is an antiaging agent.

3. A composition which contains (a) an organic material and (b) at least one type of condensed heterocyclic compound as set forth in claim 1.

4. The composition as set forth in claim 3, wherein said ingredient (a) is a synthetic polymer.

5. The composition as set forth in claim 3, wherein said ingredient (a) is a synthetic rubber.

6. The composition as set forth in claim 3, wherein said ingredient (a) is acrylic rubber or hydrogenated nitrile rubber.

7. The composition as set forth in claim 3, wherein said ingredient (a) is acrylic rubber.

8. The condensed heterocyclic compound as set forth in claim 1, wherein the condensed heterocyclic compound shown in formula (I) is a condensed heterocyclic compound shown in formula (II), formula (III), formula (VI) or formula (VII):

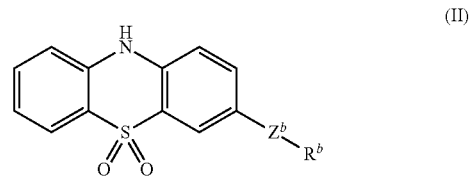

(II)

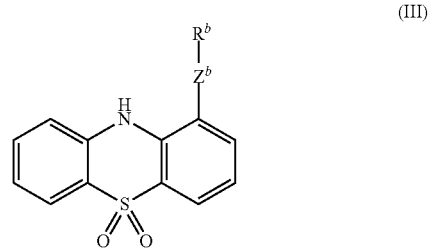

(III)

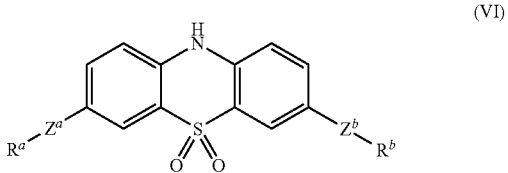

(VI)

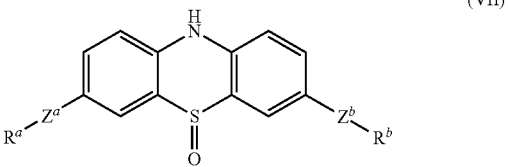

(VII)

wherein, in the formulas, —Z$^a$—R$^a$ and —Z$^b$—R$^b$ independently represent α-methylbenzyl groups, α,α-dimethylbenzyl groups, phenylsulfonyl groups, or 4-methylphenylsulfonyl groups.

9. The condensed heterocyclic compound as set forth in claim 8, wherein the condensed heterocyclic compound shown in formula (I) is a condensed heterocyclic compound shown in formula (X), formula (XI) or formula (XII):

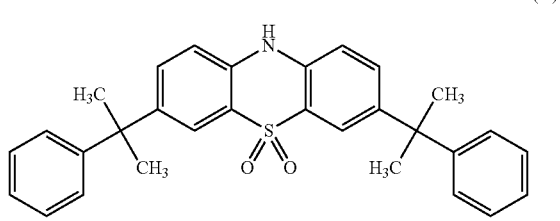

(X)

-continued

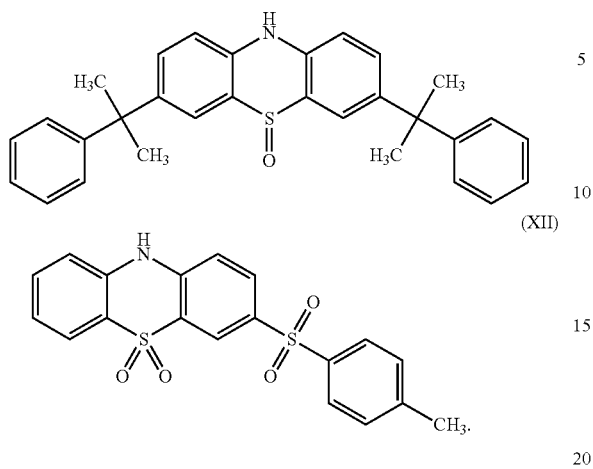

10. The condensed heterocyclic compound as set forth in claim 8, which is an antiaging agent.

11. The condensed heterocyclic compound as set forth in claim 9, which is an antiaging agent.

12. A composition which contains (a) an organic material and (b) at least one type of condensed heterocyclic compound as set forth in claim 8.

13. A composition which contains (a) an organic material and (b) at least one type of condensed heterocyclic compound as set forth in claim 9.

* * * * *